United States Patent [19]

Hodakowski

[11] 4,409,153
[45] Oct. 11, 1983

[54] O-(2-ARYL-3-OXO-1-CYCLOHEXENYL) PHOSPHATES

[75] Inventor: Leonard E. Hodakowski, St. Albans, W. Va.

[73] Assignee: Union Carbide Corporation, Danbury, Conn.

[21] Appl. No.: 351,419

[22] Filed: Feb. 23, 1982

Related U.S. Application Data

[63] Continuation of Ser. No. 134,865, Mar. 28, 1980, abandoned.

[51] Int. Cl.³ .................. C07F 9/177; A01N 57/12
[52] U.S. Cl. .................................. 260/946; 71/86; 71/87; 424/214; 260/972
[58] Field of Search ........................... 260/946

[56] References Cited

U.S. PATENT DOCUMENTS 3,784,605  1/1974  Durden et al. ............. 260/590
3,803,240  4/1974  Durden et al. ............. 260/590
4,209,532  6/1980  Wheeler ..................... 424/331

FOREIGN PATENT DOCUMENTS 1923103  2/1973  Fed. Rep. of Germany ...... 260/946

Primary Examiner—Anton H. Sutto
Attorney, Agent, or Firm—C. J. Vicari; Wm. R. Moran; J. A. Shedden

[57] ABSTRACT

Enol-phosphorous esters of 2-aryl-1,3-cycloalkanedione compounds which exhibit outstanding pesticidal, miticidal, ovicidal and herbicidal activity.

5 Claims, No Drawings

O-(2-ARYL-3-OXO-1-CYCLOHEXENYL) PHOSPHATES

This application is a continuation of our prior U.S. application Ser. No. 134,865, filing date Mar. 28, 1980, now abandoned.

This invention relates to novel enol-phosphorous esters of 2-aryl-1,3-cycloalkanediones and methods of preparing same. In another aspect this invention is directed to miticidal, pesticidal, mite ovicidal, post-emergent herbicidal and pre-emergent herbicidal compositions comprising an acceptable carrier and a pesticidally effective amount of a compound of this invention, as well as, to methods of controlling mites and plant pests which comprises subjecting the mites, the eggs of mites and the plant pests to a pesticidally effective amount of a compound of this invention.

More particularly, this invention relates to compounds of the formula:

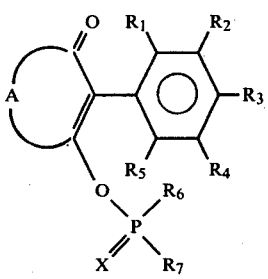

wherein:
R₁ is alkyl, haloalkyl, halogen or polyhaloalkyl;
R₂, R₃, R₄ and R₅ are individually hydrogen, nitro, polyhaloalkyl, halogen, cyano, alkyl, alkoxy, alkylthio, alkylsulfinyl, alkylsulfonyl, alkanoyl, amido, amino or haloalkyl;
A is alkylene or an alkenylene chain containing two to three carbon atoms which can be substituted by one or more substituents which may be the same or different selected from:
  (a) substituents containing from 1 to ten aliphatic carbon atoms selected from alkyl, alkenyl, cycloalkyl or cycloalkenyl groups, which groups can be further substituted with one or more cyano, halogen, nitro alkoxy, aryloxy, alkylthio, arylthio, alkylsulfinyl, arylsulfinyl, alkylsulfonyl, acylamido, or dialkylamino substituents in any combination; and a phenyl group which can be substituted by one or more alkyl, alkenyl, cycloalkyl, cycloalkenyl, cyano, halogen, nitro, alkoxy, aryloxy, alkythio, arylthio, alkylsulfinyl, arylsulfinyl, alkylsulfonyl, arylsulfonyl, acylamido or dialkylamino substituents in any combination, or
  (b) a divalent alkylene or alkenylene group having from 2 to 20 carbon atoms completing a 3, 4, 5, 6 or 7 membered carbon ring; wherein the said formed 6-membered ring may optionally be aromatic;
X=O or S;
R₆ and R₇ can be the same or different and individually can be alkyl, alkoxy, alkylthio, halogen, alkylthioalkyl, alkylsulfinyl, alkylsulfonyl, dialkylamino, haloalkyl, cycloalkyl, aryl, aryloxy;
with the proviso that R₁, R₂, R₃, R₄ and R₅ individually may not include more than ten aliphatic carbon atoms.

The following pesticidally, miticidally, mite ovicidally and herbicidally active compounds are illustrative of compounds within the purview of the generic formula set forth above, all of which can be conveniently prepared by the processes of this invention simply by selecting appropriate reactants.

O-[2-(2'-methylphenyl)-5,5-dimethyl-3-oxo-1-cyclohexenyl]-O-ethyl-S-n-propyl thiophosphate.
O-[2-(2'-methylphenyl)-5,5-dimethyl-3-oxo-1-cyclohexenyl]-O-ethyl-S-n-propyl phosphorodithioate.
O-[2-(2'-methylphenyl)-5,5-dimethyl-3-oxo-1-cyclohexenyl]-O-ethyl-S-n-butylthiophosphate.
O-[2-(2'-methylphenyl)-5,5-dimethyl-3-oxo-1-cyclohexenyl]-O,O-diethyl phosphate.
O-[2-(2'-methylphenyl)-5,5-dimethyl-3-oxo-1-cyclohexenyl]-O,O-diethyl thionophosphate.
O-[2-(2'-methylphenyl)-5,5-dimethyl-3-oxo-1-cyclohexenyl]-N,N,N,N-tetramethyl phosphoro diamidate.
O-[2-(2'-methylphenyl)-5,5-dimethyl-3-oxo-1-cyclohexenyl]-O,O-diphenyl phosphate.
O-[2-(2'-methylphenyl)-5,5-dimethyl-3-oxo-1-cyclohexenyl]-O-ethyl-thionoethanephosphonate.
O-[2-(2'-methylphenyl)-5,5-dimethyl-3-oxo-1-cyclohexenyl]-O-ethyl-O-n-propyl thionophosphate.
O-[2-(2'-methylphenyl)-5,5-dimethyl-3-oxo-1-cyclohexenyl]-O-ethyl-thionobenzenephosphonate.
O-[2-(2'-methylphenyl)-5,5-dimethyl-3-oxo-1-cyclohexenyl]-O-ethyl-N-isopropyl phosphoramidate.
O-[2-(2',4'-dimethylphenyl)-5,5-dimethyl-3-oxo-1-cyclohexenyl]-O-ethyl-S-n-propyl thiophosphate.
O-[2-(2',4'-dimethylphenyl)-5,5-dimethyl-3-oxo-1-cyclohexenyl]-O-ethyl-S-n-propyl phosphorodithioate.
O-[2-(2',4'-dimethylphenyl)-5,5-dimethyl-3-oxo-1-cyclohexenyl]-O-ethyl-S-n-butyl thiophosphate.
O-[2-(2',4'-dimethylphenyl)-5,5-dimethyl-3-oxo-cyclohexenyl]-O,O-diethyl phosphate.
O-[2-(2',4'-dimethylphenyl)-5,5-dimethyl-3-oxo-1-cyclohexenyl)-O-ethyl-O-n-propyl thionophosphate.
O-[2-(2',4'-dimethylphenyl)-5,5-dimethyl-3-oxo-1-cyclohexenyl]-O-ethyl-thionobenzenephosphonate.
O-[2-(3'-methylphenyl)-5,5-dimethyl-3-oxo-1-cyclohexenyl]-O-ethyl-S-n-propyl thiophosphate.
O-[2-(4'-methylphenyl)-5,5-dimethyl-3-oxo-1-cyclohexenyl]-O-ethyl-S-n-propyl thiophosphate.
O-[2-(3',4'-dimethylphenyl)-5,5-dimethyl-3-oxo-1-cyclohexenyl]-O-ethyl-S-n-propyl thiosphosphate.
O-[2-(2'-methyl-4'-methoxyphenyl)-5,5-dimethyl-3-oxo-1-cyclohexenyl]-O-ethyl-S-n-propyl thiophosphate.
O-[2-(2',4',6'-trimethylphenyl)-5,5-dimethyl-3-oxo-1-cyclohexenyl]-O-ethyl-S-n-propyl thiophosphate.
O-[2-(2'-ethylphenyl)-5,5-dimethyl-3-oxo-1-cyclohexenyl]-O-ethyl-S-n-propyl thiophosphate.
O-[2-(2'-chlorophenyl)-5,5-dimethyl-3-oxo-1-cyclohexenyl]-O-ethyl-S-n-propyl thiophosphate.
O-[2-(3'-chlorophenyl)-5,5-dimethyl-3-oxo-1-cyclohexenyl]-O-ethyl-S-n-propyl thiophosphate.
O-[2-(4'-chlorophenyl)-5,5-dimethyl-3-oxo-1-cyclohexenyl]-O-ethyl-S-n-propyl thiophosphate.
O-[2-(4'-chlorophenyl)-5,5-dimethyl-3-oxo-1-cyclohexenyl]-O-ethyl-S-n-propyl phosphorodithioate.
O-[2-(4'-chlorophenyl)-5,5-dimethyl-3-oxo-1-cyclohexenyl]-O-ethyl-S-n-butyl thiophosphate.
O-[2-(4'-chlorophenyl)-5,5-dimethyl-3-oxo-1-cyclohexenyl]-O-ethyl-thionoethane phosphonate.

O-[2-(2',4'-dichlorophenyl)-5,5-dimethyl-3-oxo-1-cyclohexenyl]-O-ethyl-S-n-propyl thiophosphate.
O-[2-(3',4'-dichlorophenyl)-5,5-dimethyl-3-oxo-1-cyclohexenyl]-O-ethyl-S-n-propyl thiophosphate.
O-[2-(2'-methyl-4'-chlorophenyl)-5,5-dimethyl-3-oxo-1-cyclohexenyl]-O-ethyl-S-n-propyl thiophosphate.
O-[2-(2'-trifluoromethyl-4'-chlorophenyl)-5,5-dimethyl-3-oxo-1-cyclohexenyl]-O-ethyl-S-n-propyl thiophosphate.
O-[2-(2',4',6'-trimethylphenyl)-5-isopropyl-3-oxo-1-cyclohexenyl]-O-ethyl-S-n-propyl thiophosphate.
O-[8-(2'-methylphenyl)-9-oxo-spiro (4.5)-7-decen-7-yl]-O-ethyl-S-n-propyl thiophosphate.
O-[2-(2'-methylphenyl)-5-methyl-5-n-pentyl-3-oxo-1-cyclohexenyl]-O-ethyl-S-n-propyl thiophosphate.
O-[2-(2',5'-dimethylphenyl)-3-oxo-1-cyclopentenyl]-O-ethyl-S-n-propyl thiophosphate.
O-[2-(2',4'-dichlorophenyl)-3-oxo-1-cyclopentenyl]-O-ethyl-S-n-propyl thiophosphate.
O-[2-(2',5'-dimethylphenyl-3-oxo-4,5,6,7-tetrahydro-1H-Inden-3-4]-O-ethyl-S-n-propyl thiophosphate.

All compounds within the purview of the above generic formula exhibit pesticidal, miticidal, mite ovicidal, pre-emergent herbicidal and post-emergent herbicidal activity to a lesser or greater extent. Some of these compounds exhibit very high levels of miticidal, mite ovicidal or herbicidal activity in extremely small dosages while others require larger dosages to be pesticidally effective. In general, the compounds of this invention that exhibit the highest order of herbicidal activity also exhibit the highest order of miticidal and mite ovicidal activity. Miticidal and mite ovicidal activity is greatest in those compounds having a hydrogen, alkyl or halogen at an ortho position of the 2-phenyl moiety, the other ortho substituent being an alkyl or halogen group. Outstanding active compounds are those in which the ortho substituents are relatively small groups, such as hydrogen, methyl or halogen.

In addition, alkyl or halogen substitution at an ortho position while the other ortho substitute is hydrogen, or alkyl in the 2-phenyl moiety and the para position is alkyl or halogen also provide superior results with respect to miticidal activity.

Most effective results are obtained when the phosphorylating group is of the

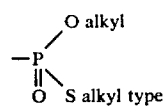

S alkyl type wherein the alkyl moiety is $C_1$ to $C_8$.

Preferred because of their higher levels of pesticidal, miticidal, mite ovicidal and herbicidal activity are the compounds of this invention in which, $R_2$, $R_3$, $R_4$ and $R_5$ are individually hydrogen, alkyl, halogen and alkoxy;
$R_1$ is alkyl or halogen.

The most active and particularly preferred compounds are those in which, $R_2$, $R_3$, $R_4$ and $R_5$ are individually hydrogen, methyl, methoxy, or halogen;
$R_1$ is methyl or halogen; with the preferred values
$R_2$, $R_3$, $R_4$ and $R_5$ being individually hydrogen, methyl or ethyl, chlorine and methoxy.

Compounds which are most preferred also include those in which A represents an alkylene chain containing three carbon atoms and which conform to the general structure shown below:

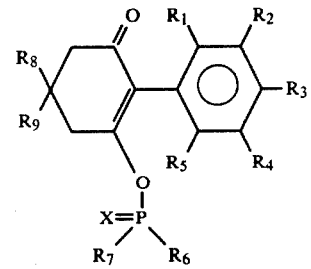

wherein $R_1$–$R_7$ and X are as above defined and wherein $R_8$ and $R_9$ are hydrogen or alkyl of 1 to 6 carbon atoms.

The novel enol esters of 2-aryl-1,3-cyclohexanedione compounds of this invention can be conveniently prepared by the following reaction scheme:

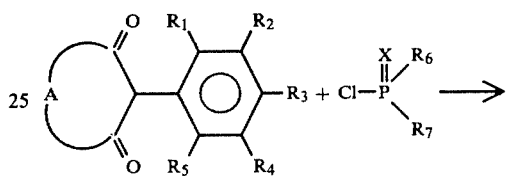

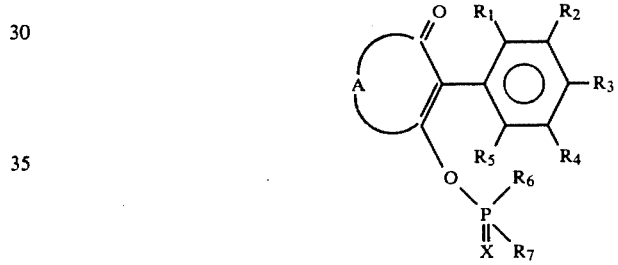

wherein the values of $R_1$–$R_7$, X and A are as indicated above.

In this reaction sequence one equivalent of the appropriate dione is reacted with an appropriate chloro phosphorus compound in the presence of at least one equivalent of an acid acceptor, preferably in an inert solvent.

The acid acceptor utilized in this reaction scheme can be either an organic or inorganic base. Illustrative of organic bases that are useful acid acceptors include tertiary amines, such as triethylamine, pyridine, trimethylamine or 1,4-diazobicyclo (2.2.2) octane; bases such as sodium carbonate, potassium carbonate, and sodium hydroxide are illustrative of inorganic bases that are useful acid acceptors.

In general, any organic solvent that is inert to the reactants or reaction conditions may be employed in the reaction scheme shown above. Illustrative of organic solvents which are generally suitable for use in conducting these reactions are saturated, unsaturated and aromatic hydrocarbons, e.g. hexane, cyclohexane, octane, cyclohexane, dodecane, naptha, decalin, kerosene, cycoheptane, benzene, toluene, xylene, naphthylene, or the like; ethers such as dioxane, tetrahydrofuran, diethyl ether, tetrahydropycan, 1,2-dimethoxybenzene, the dialkyl ethers of ethylene glycol, of propylene glycol or chlorinated aliphatic hydrocarbons, as, for example, chloroform, dichloromethane, 1,1-dichloroethane, carbon tetrachloride, and the like.

The reactions illustrated by the general scheme given above may also be conducted in a solvent which functions as an acid acceptor. Illustrative of such multifunctional solvents are N,N-dimethylaniline, pyridine, α-picoline, any lutidine collodine or any like aromatic or heterocyclic tertiary amine compound.

The reactions illustrated by the general scheme given above are neither temperature or pressure sensitive and can be conducted over a broad temperature and pressure range to yield the desired product. Preferably, these reactions are conducted at a temperature of −40° C. to about 120° C. and at atmospheric or autogeneous pressure.

The phosphorus halides utilized as reactants in the above reaction scheme generally are known materials which can be obtained from commercial sources or prepared in accordance with conventional methods known to those skilled in the art.

Several of the 2-aryl-1,3-cycloalkanediones utilized as reactants in the above synthetic scheme are known compounds. The 2-aryl-1,3-cyclopentanediones may be prepared by the base-promoted cyclization of ethyl-5-aryl-4-ketopentanoates and the 2-aryl-1,3-cyclohexanediones may be prepared by the base promoted cyclization of ethyl 6-aryl-5-ketohexanoates.

The following specific examples are presented to more particularly illustrate the novel process of this invention and its use in preparing the novel compounds of this invention.

The starting diones that were employed in the following examples were prepared according to the procedure described in the copending application of Thomas N. Wheeler, filed on Mar. 28, 1977, Ser. No. 781,781, and assigned to a common assignee.

EXAMPLE 1

Preparation of
O-[2-(2'-methylphenyl)-5,5-dimethyl-3-oxo-1-cyclohexenyl]-O-ethyl-S-n-propyl thiophosphate A 100 ml flask was equipped with a magnetic stirrer, condenser, drying tube and addition funnel. The glassware was dried thoroughly and charged with 4.6 g (0.020 mole) of 2-(2-methylphenyl)-5,5-dimethyl-1,3-cyclohexanedione, 60 ml of methylene chloride, and 2.1 g (0.021 mole) of triethylamine. The material was stirred at room temperature for 30 minutes and then cooled to 15° C. using a water/ice bath. To this was added 4.1 g (0.020 mole) of O-ethyl-S-n-propyl thiochlorophosphate. The reaction mixture was heated to 40° C. for 4 hours and then cooled to room temperature and the methylene chloride removed on the rotary evaporator. Ethyl ether was added and the triethylamine hydrochloride salt was filtered. The filtrate was washed with 8 N sodium hydroxide (1×300 ml), water (2×300 ml), 4 percent hydrochloric acid (1×200 ml), water (2×300 ml), 8 N sodium hydroxide (1×300 ml), water (2×200 ml), dried over anhydrous magnesium sulfate, filtered and concentrated on rotary evaporator. The residue gave 5.9 g of a viscous oil as the desired product ($n_D^{23}$ 1.5340).

Calcd for $C_{20}H_{29}O_4PS$: C, 60.61; H, 7.32. Found: C, 60.52; H, 7.46.

EXAMPLE II

Preparation of O-[2-(2'-methylphenyl)-5,5-dimethyl-3-oxo-1-cyclohexenyl]-O,O-diethyl thionophosphate A 100 ml flask was equipped with a magnetic stirrer, condenser, drying tube and addition funnel. The glassware was dried thoroughly and charged with 6.9 g (0.30 mole) of 2-(2'-methylphenyl)-5,5-dimethyl-1, 3-cyclohexanedione, 50 ml acetonitrile, and 3.1 g (0.031 mole) of triethylamine. The material was stirred at room temperature for 30 minutes and then cooled to 15° C. using a water/ice bath. To this was charged 5.7 g (0.030 mole) of O,O-diethyl chlorothio phosphate. The reaction mixture was heated to 40° C. for 4 hours and then cooled to room temperature and the acetonitrile removed on the rotary evaporator. The residue was taken up in 200 ml of ethyl ether and filtered. The filtrate was washed with 1 percent hydrochloric acid, 4 N sodium hydroxide and finally water. The ether layer was dried over anhydrous magnesium sulfate, filtered and concentrated on rotary evaporator. The residue gave 4.5 g of a viscous oil as the desired product. ($n_D^{22}$—1.5338).

(Calcd for $C_{19}H_{27}O_4PS$: C, 59.68; H, 7.07. Found: C, 59.91; H, 6.85.

The following examples 3–33 were prepared in a manner similar to Examples 1 and 2. Table I indicates the physical data for each of the compounds prepared.

TABLE I

| Structure & Example | Refractive Index (°C.) | Molecular Formula | Calculated C | Calculated H | Found C | Found H |
|---|---|---|---|---|---|---|
| Example No. 3 | 1.5533 (22°) | $C_{20}H_{29}O_3PS_2$ | 58.25 | 7.04 | 61.76 | 6.86 |
| Example No. 4 | 1.5335 (22°) | $C_{21}H_{31}O_4PS$ | 61.46 | 7.56 | 61.94 | 7.54 |
| Example No. 5 | 1.5140 (22°) | $C_{19}H_{27}O_5P$ | 62.30 | 7.38 | 62.57 | 7.35 |

TABLE I-continued

| Structure & Example | Refractive Index (°C.) | Molecular Formula | Calculated C | Calculated H | Found C | Found H |
|---|---|---|---|---|---|---|
| Example No. 6 | | $C_{19}H_{29}N_2O_3P$ | 62.64 | 7.97 | 62.91 | 7.89 |
| Example No. 7 | 1.5651 (22°) | $C_{27}H_{27}O_5P$ | 70.13 | 5.84 | 70.13 | 5.80 |
| Example No. 8 | 1.5418 (22°) | $C_{19}H_{27}O_3PS$ | 62.30 | 7.38 | 61.90 | 7.34 |
| Example No. 9 | 1.5310 (24°) | $C_{20}H_{29}O_4PS$ | 60.61 | 7.32 | 61.40 | 7.30 |
| Example No. 10 | 1.5705 (24°) | $C_{23}H_{27}O_3PS$ | 66.67 | 6.52 | 66.48 | 6.60 |
| Example No. 11 | 1.5335 (23°) | $C_{21}H_{31}O_4PS$ | 61.46 | 7.56 | 61.21 | 7.51 |
| Example No. 12 | 1.5548 (22°) | $C_{21}H_{31}O_3PS_2$ | 59.15 | 7.28 | 59.48 | 7.31 |

TABLE I-continued

| Structure & Example | Refractive Index (°C.) | Molecular Formula | Calculated C | Calculated H | Found C | Found H |
|---|---|---|---|---|---|---|
| Example No. 13 (structure with OC₂H₅, S—n-C₃H₇) | 1.5254 (23°) | C₂₂H₃₃O₄PS | 62.26 | 7.78 | 61.27 | 7.81 |
| Example No. 14 (structure with OC₂H₅, S—n-C₄H₉) | 1.5320 (22°) | C₂₀H₂₉O₄PS | 60.61 | 7.32 | 60.23 | 7.33 |
| Example No. 15 (structure with OC₂H₅, OC₂H₅) | 1.5295 (23°) | C₂₁H₃₁O₄PS | 61.46 | 7.56 | 62.73 | 7.52 |
| Example No. 16 (structure with OC₂H₅, O—n-C₃H₇) | 1.5655 (23°) | C₂₄H₂₉O₃PS | 67.29 | 6.78 | 66.89 | 6.72 |
| Example No. 17 (structure with OC₂H₅, S—n-C₃H₇) | 1.5328 (22°) | C₂₀H₂₉O₄PS | 60.61 | 7.32 | 60.87 | 7.48 |
| Example No. 18 (structure with OC₂H₅, S—n-C₃H₇) | 1.5355 (23°) | C₂₀H₂₉O₄PS | 60.61 | 7.32 | 61.08 | 7.20 |
| Example No. 19 | 1.5275 (24°) | C₂₁H₃₁O₄PS | 61.46 | 7.56 | 61.30 | 7.99 |

TABLE I-continued

| Structure & Example | Refractive Index (°C.) | Molecular Formula | Calculated C | Calculated H | Found C | Found H |
|---|---|---|---|---|---|---|
| [Example No. 20 structure: 4,4-dimethyl-2-(3,4-dimethylphenyl)-6-[(ethoxy)(n-propylthio)phosphoryloxy]cyclohex-2-en-1-one] | | | | | | |
| Example No. 20 | 1.5301 (24°) | $C_{21}H_{31}O_5PS$ | 59.15 | 7.28 | 56.80 | 7.05 |
| [Example No. 21 structure: with 2-methyl-4-methoxyphenyl] | | | | | | |
| Example No. 21 | 1.5410 (22°) | $C_{19}H_{26}ClO_4PS$ | 54.74 | 6.24 | 54.83 | 6.37 |
| [Example No. 22 structure: 2-chlorophenyl] | | | | | | |
| Example No. 22 | 1.5420 (22°) | $C_{19}H_{26}ClO_4PS$ | 54.74 | 6.24 | 55.08 | 6.45 |
| [Example No. 23 structure: 3-chlorophenyl] | | | | | | |
| Example No. 23 | 1.5424 (23°) | $C_{19}H_{26}ClO_4PS$ | 54.74 | 6.24 | 54.76 | 6.38 |
| [Example No. 24 structure: 4-chlorophenyl with P=S] | | | | | | |
| Example No. 24 | 1.5605 (23°) | $C_{19}H_{26}ClO_3PS_2$ | 52.72 | 6.01 | 52.55 | 5.98 |
| [Example No. 25 structure: 4-chlorophenyl with S-n-C4H9] | | | | | | |
| Example No. 25 | 1.5345 (22°) | $C_{20}H_{28}ClO_4PS$ | 55.75 | 6.50 | 55.50 | 6.47 |
| Example No. 26 | 1.5543 (22°) | $C_{18}H_{24}ClO_3PS$ | 55.89 | 6.21 | 56.56 | 6.03 |

TABLE I-continued
| Structure & Example | Refractive Index (°C.) | Molecular Formula | Calculated C | Calculated H | Found C | Found H |
|---|---|---|---|---|---|---|
| Example No. 27 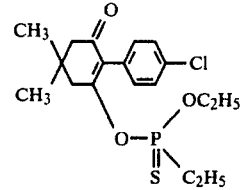 | 1.5465 (21°) | C₁₉H₂₅Cl₂O₄PS | 50.55 | 5.54 | 50.98 | 5.31 |
| Example No. 28 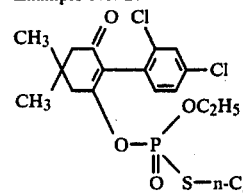 | 1.5486 (23°) | C₁₉H₂₅Cl₂O₄PS | 50.55 | 5.54 | 50.73 | 5.70 |
| Example No. 29 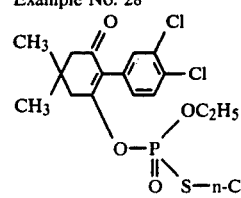 | 1.5355 (23°) | C₂₀H₂₈ClO₄PS | 55.75 | 6.50 | 54.50 | 6.7 |
| Example No. 30 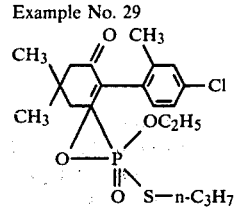 | 1.5460 (22°) | C₂₂H₃₁O₄PS | 62.56 | 7.35 | 62.32 | 7.39 |
| Example No. 31 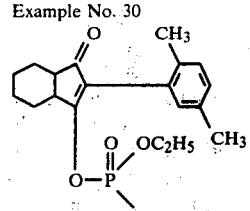 | 1.5605 (22°) | C₁₆H₁₉Cl₂O₄PS | 46.94 | 4.65 | 47.42 | 5.04 |
| Example No. 32 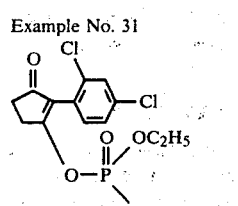 | 1.5250 (22°) | C₂₄H₃₇O₄PS | 63.72 | 8.19 | 63.80 | 8.39 |
2-arylcyclohexanedione
| Example No. 33 | 1.5433 (22°) | C₂₂H₃₁O₄PS | 62.56 | 7.34 | 62.25 | 7.35 |

TABLE I-continued

| | Refractive | Molecular | Calculated | | Found | |
|---|---|---|---|---|---|---|
| Structure & Example | Index (°C.) | Formula | C | H | C | H |

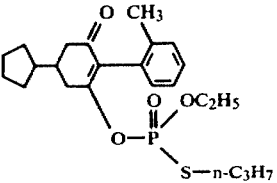

The following compounds corresponding to Examples 34–40 were also prepared according to the procedure of Example 1 and 2 and their structures were confirmed by spectral analysis:

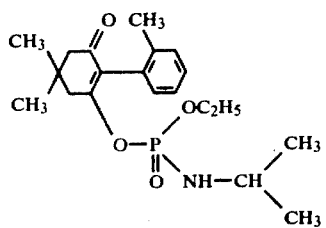

Example No. 34

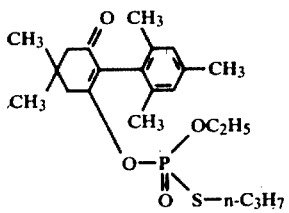

Example No. 35

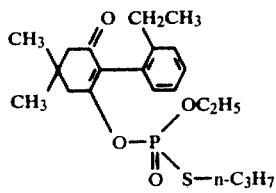

Example No. 36

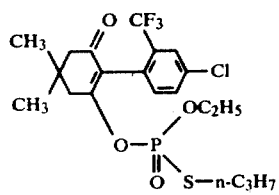

Example No. 37

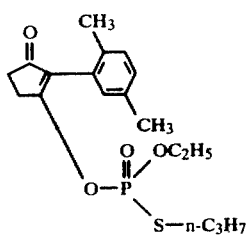

Example No. 38

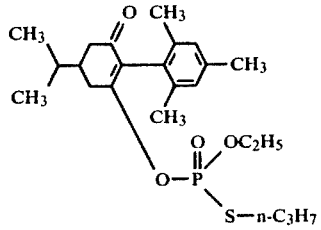

Example No. 39

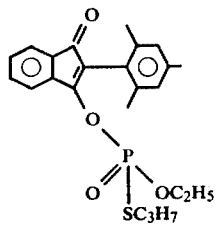

Example No. 40

Selected enol-phosphorous esters of 2-aryl-1,3-cyclohexanedione compounds, representative of those useful in accordance with this invention were tested with respect to their miticidal, mite ovicidal and pre-emergent and post-emergent herbicidal activity.

Suspensions of the test compounds were prepared by dissolving one gram of compound in 50 milliliters of acetone in which had been dissolved 0.1 gram (10 percent of the weight of compound) of an alkylphenoxy-ethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described hereinbelow were obtained by diluting the stock suspension with water. The test procedures were as follows:

MITE FOLIAGE SPRAY TEST

Adults and nymphal stages of the two-spotted mite (*Tetranychus urticae* (Koch)), reared on Tendergreen bean plants at 80±5° F. and 50±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psig. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5° F. and 50±5 percent relative humidity for four days, after which, a mortality count of mobile forms was made on the leaves of the test plants. Any individual which was capable of locomotion upon prodding was considered living.

MITE OVICIDE TEST

The test organism was the egg of the two-spotted mite (*Tetranychus urticae* (Koch)), as obtained from adults reared on Tendergreen bean plants under controlled conditions of 80±5° F. and 50±5 percent relative humidity. Heavily infested leaves from a stock culture were placed on the primary leaves of two bean plants six to eight inches in height, growing in a two-and-a-half inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The potted plants (one pot per compound) were placed on a revolving turntable and sprayed with 100-110 milliliters of test compound formulation by use of a DeVilbis spray gun set at 40 psig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80±5° F. and 50±5 percent relative humidity for four days, after which a microscopic examination was made of unhatched (dead) and hatched (living) eggs. The test procedures were as follows:

BEAN APHID

Adults and nymphal stages of the bean aphid (*Aphis fabae* Scop.) reared on potted dwarf nasturtium plants at 65°-70° F. and 50±5 percent relative humidity, constituted with test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test comound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

SOUTHERN ARMYWORM

Larvae of the southern armyworm (SAW) (*Spodoptera eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead.

MEXICAN BEAN BEETLE

Fourth instar larvae of the Mexican bean beetle (MBB), (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

HOUSEFLIES

Four to six day old adult house flies (HF) (*Musca domestica*, L.), reared according to the specifications of the Chemical Specialties Manufacturing Association (Blue Book, McNair-Dorland Co., N.Y. 1954; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard foot strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

In these tests the pesticidal activity of the compounds against the above species was rated as follows:
A = Excellent Control
B = Partial Control
C = No Control

PRELIMINARY HERBICIDE SEED GERMINATION TEST

The following seeds were used in this test:
Perennial rye grass—*Solium perenne*
Mustard—*Brassica pincea* var. *foliosa* (Florida broadleaf)
A seed-oil mixture was prepared as follows:
196 cc. Rye grass seed
75 cc. Mustard seed
18,000 cc. Sifted, fairly dry soil The above mixture was rolled in 5 gallon containers for approximately one-half hour on ball mill to insure uniform mixing of seeds and soil. For each compound four 3-inch pots were filled with soil to within 1½ inches of top of pots. To these pots were added 70 cc. of the mixture. The seed-soil mixture was tamped firmly and the pots were removed to the greenhouse and watered lightly. About 2 hours after planting, 25 milliliters of the test formulation were added to the pots for each soil-seed mixture, i.e., one replicate of each seed mixture per concentration. An equal volume of a water solution containing acetone and an emulsifier in the same concentration as the herbicidal mixture but without the candidate herbicide was also added to each of the soil-seed mixtures. These pots are used as check or control units. The test compounds were formulated by standard procedure of dissolving in acetone, addition of an emulsifier, and dilution with water. Tests were conducted on all compositions at low concentration (100 ppm.). Certain compositions were also tested at high concentration (1000 ppm). The pots were held in the greenhouse and watered lightly until results were taken. Ten to twelve days after application of chemical, injury was noted for each species by comparing treated vs. untreated pots. Ratings were made at both the high and the low concentrations (1000 ppm and 100 ppm) according to the following designations:
5 = no seedlings emerged
4 = few seedlings emerged and/or very severe stunting
3 = moderate reduction in stand and/or moderate stunting.
2 = very slight reduction in stand and/or slight stunting
1 = no injury; seedlings appear no different with respect to stand or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below.

| Example Number | Bean Aphid | Mite Adult | Mite Eggs | SAW | MBB | HF | Post-Emergence Herbicidal | | | Pre-Emergence Herbicidal | |
|---|---|---|---|---|---|---|---|---|---|---|---|
| | | | | | | | Corn | Cotton | Soybean | Rye | Mustard |
| 1 | A | A | A | A | A | A | 5 | 1 | 2 | 5 | 3 |
| 2 | C | A | A | C | A | A | 1 | 1 | 1 | 1 | 1 |
| 3 | C | A | A | C | C | B | 2 | 1 | 1 | 2 | 1 |
| 4 | A | A | A | A | A | B | 3 | 1 | 2 | 5 | 2 |
| 5 | C | A | A | C | C | C | 3 | 1 | 2 | 5 | 2 |
| 6 | B | A | C | C | C | C | 1 | 1 | 3 | 1 | 1 |
| 7 | C | A | A | C | C | C | 1 | 1 | 1 | 1 | 1 |
| 8 | C | A | A | B | C | A | 1 | 1 | 1 | 1 | 1 |
| 9 | C | A | A | C | C | B | 1 | 1 | 1 | 1 | 1 |
| 10 | C | A | A | B | C | C | 2 | 1 | 2 | 1 | 1 |
| 11 | A | A | A | A | A | B | 3 | 1 | 1 | 5 | 2 |
| 12 | A | A | A | A | B | A | 2 | 1 | 1 | 5 | 1 |
| 13 | A | A | A | A | A | B | 5 | 1 | 2 | 1 | 1 |
| 14 | C | A | A | C | B | C | 2 | 1 | 2 | 1 | 1 |

-continued

| Example Number | Bean Aphid | Mite Adult | Mite Eggs | SAW | MBB | HF | Post-Emergence Herbicidal | | | Pre-Emergence Herbicidal | |
|---|---|---|---|---|---|---|---|---|---|---|---|
| | | | | | | | Corn | Cotton | Soybean | Rye | Mustard |
| 15 | C | A | A | C | C | C | 1 | 1 | 1 | 4 | 1 |
| 16 | C | B | C | C | C | C | 1 | 1 | 1 | 5 | 1 |
| 17 | A | A | A | A | A | B | 1 | 1 | 1 | 1 | 1 |
| 18 | A | A | A | A | A | B | 2 | 1 | 2 | 2 | 1 |
| 19 | B | A | B | C | B | C | 2 | 2 | 2 | 1 | 1 |
| 20 | A | A | A | C | A | A | 3 | 1 | 2 | 3 | 1 |
| 21 | A | A | A | A | A | A | 3 | 2 | 2 | 5 | 2 |
| 22 | A | A | A | A | A | A | 2 | 1 | 2 | 1 | 1 |
| 23 | A | A | A | A | A | A | 3 | 1 | 2 | 3 | 1 |
| 24 | A | A | A | A | A | A | 2 | 1 | 1 | 1 | 1 |
| 25 | A | A | A | A | A | B | 3 | 1 | 2 | 3 | 1 |
| 26 | C | A | A | B | B | B | 1 | 1 | 1 | 1 | 1 |
| 27 | A | A | A | A | A | A | 5 | 1 | 2 | 5 | 3 |
| 28 | A | A | A | A | A | A | 3 | 2 | 2 | 1 | 1 |
| 29 | A | A | A | A | A | A | | | | 5 | 3 |
| 30 | A | A | A | A | A | A | 5 | 1 | 1 | 1 | 1 |
| 31 | A | A | C | C | C | B | 2 | 1 | 1 | 5 | 2 |
| 32 | A | A | C | A | A | A | 3 | 1 | 2 | 1 | 1 |
| 33 | A | A | A | A | A | C | 4 | 1 | 2 | 3 | 2 |
| 34 | C | A | C | C | C | B | | | | | |
| 35 | A | A | C | A | A | B | | | | | |
| 36 | A | A | A | A | A | A | | | | 5 | 1 |
| 37 | C | A | C | C | C | C | | | | 1 | 1 |
| 38 | C | A | C | C | C | B | | | | 1 | 1 |
| 39 | A | A | A | A | A | B | | | | | |
| 40 | A | A | A | A | A | A | 2 | 3 | 2 | 5 | 3 |

It will be understood that the plant species employed in the above tests are merely representative of a wide variety of plant pest that can be controlled by the use of the compounds of this invention. The compounds contemplated in this invention may be applied as mite ovicides, miticides and herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. It will be appreciated that the compounds of this invention can also be used in combination with other biologically active compounds.

What is claimed is:

1. O-[2-(2'methylphenyl)-5,5-dimethyl-3-oxo-1-cyclohexenyl]-O-ethyl-S-n-propyl thiophosphate.

2. O-[2-(2'-methylphenyl)-5,5-dimethyl-3-oxo-1-cyclohexenyl]-O-ethyl-S-n-butylthiophosphate.

3. O-[2-(2',4'-dimethylphenyl)-5,5-dimethyl-3-oxo-1-cyclohexenyl]-O-ethyl-S-n-propyl thiophosphate.

4. O-[2-(2',4'-dichlorophenyl)-5,5-dimethyl-3-oxo-1-cyclohexenyl]-O-ethyl-S-n-propyl thiophosphate.

5. O-[2-(2'-methyl-4'-chlorophenyl)-5,5-dimethyl-3-oxo-1-cyclohexenyl]-O-ethyl-S-n-propyl thiophosphate.

* * * * *